(12) United States Patent
Wheatcroft et al.

(10) Patent No.: US 6,444,448 B1
(45) Date of Patent: *Sep. 3, 2002

(54) PRODUCTION OF β-GLUCAN-MANNAN PREPARATIONS BY AUTOLYSIS OF CELLS UNDER CERTAIN PH, TEMPERATURE AND TIME CONDITIONS

(75) Inventors: Ragini Wheatcroft; Joseph Kulandai; Robert White Gilbert; Keith James Sime; Craig Gordon Smith; Willem Hendrik Langeris, all of Melbourne (AU)

(73) Assignee: Carlton and United Breweries, Limited, Carlton Victoria (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,860
(22) PCT Filed: Jun. 28, 1996
(86) PCT No.: PCT/AU96/00401
§ 371 (c)(1), (2), (4) Date: Jun. 24, 1998
(87) PCT Pub. No.: WO97/02356
PCT Pub. Date: Jan. 23, 1997

(30) Foreign Application Priority Data
Jul. 5, 1995 (AU) .............................................. PN3982

(51) Int. Cl.$^7$ .......................... C12P 19/04; C12N 1/16; A61K 31/716
(52) U.S. Cl. .......................... 435/101; 435/99; 435/95; 435/72; 435/169; 435/170; 435/171; 435/259; 426/60; 426/62; 426/656; 424/234.1; 424/274.1; 424/278.1; 424/282.1; 424/93.5; 424/93.51; 514/54; 514/777
(58) Field of Search .......................... 435/101, 99, 95, 435/72, 169, 170, 171, 259; 426/60, 62, 656; 424/234.1, 274.1, 278.1, 282.1, 93.5, 93.51; 514/54, 777

(56) References Cited

U.S. PATENT DOCUMENTS

| | | | | |
|---|---|---|---|---|
| 3,822,250 A | * | 7/1974 | Kimura et al. | 260/209 |
| 4,122,196 A | * | 10/1978 | Robbins et al. | 426/60 |
| 4,138,479 A | * | 2/1979 | Trascheit et al. | 424/88 |
| 4,218,481 A | * | 8/1980 | Chao et al. | 426/60 |
| 4,313,934 A | * | 2/1982 | Kitamura et al. | 424/85 |
| 4,769,363 A | * | 9/1988 | Misaki et al. | 514/54 |
| 4,965,347 A | * | 10/1990 | Misaki et al. | 536/1.1 |
| 5,084,386 A | | 1/1992 | Tuse et al. | 435/101 |
| 5,223,491 A | | 6/1993 | Donzis | |
| 5,576,015 A | * | 11/1996 | Donzis | 424/442 |
| 5,702,719 A | | 12/1997 | Donzis | |
| 5,705,184 A | | 1/1998 | Donzis | |

FOREIGN PATENT DOCUMENTS

JP 53-044614 4/1978

OTHER PUBLICATIONS

*Dictionary of Microbiology and Molecular Biology*, Singleton, ed., John Wiley & Sons, pp. 289, 391, 1987.*
Pelczar et al., *Elements of Microbiology*, McGraw–Hill, Inc., p. 35, 1981.*
T.L. Babayan et al., "Isolation of Physiologically Active Mannan and Other Polysaccharides from Autolysate of Baker's Yeast.", Biotekhnologiya, No. 2, 1992, pp. 23–26, Abstract only, Database–BIOSIS, XP–002146533.
Patent Abstracts of Japan, JP 07–184595 A (Nippon Paper) Jul. 25, 1995 Derwent AN 95–287919/38.

* cited by examiner

Primary Examiner—Francisco Prats
(74) Attorney, Agent, or Firm—Foley & Lardner

(57) ABSTRACT

There is provided a method of production of an immunostimulatory β-glucan-mannan preparation, comprising the step of autolysis of cells of a microorganism at a pH of 5 to 6 and a temperature of 35 to 60° C. for 6 to 48 hours, and separating solid material roam the autolysed product.

The β-glucan-mannan preparation may be incorporated as a food component or be used as a pharmaceutical for treatment of conditions such as immuno-suppression, hypercholesterolaemia, hypoglycaemia and heavy metal excretion.

25 Claims, 1 Drawing Sheet

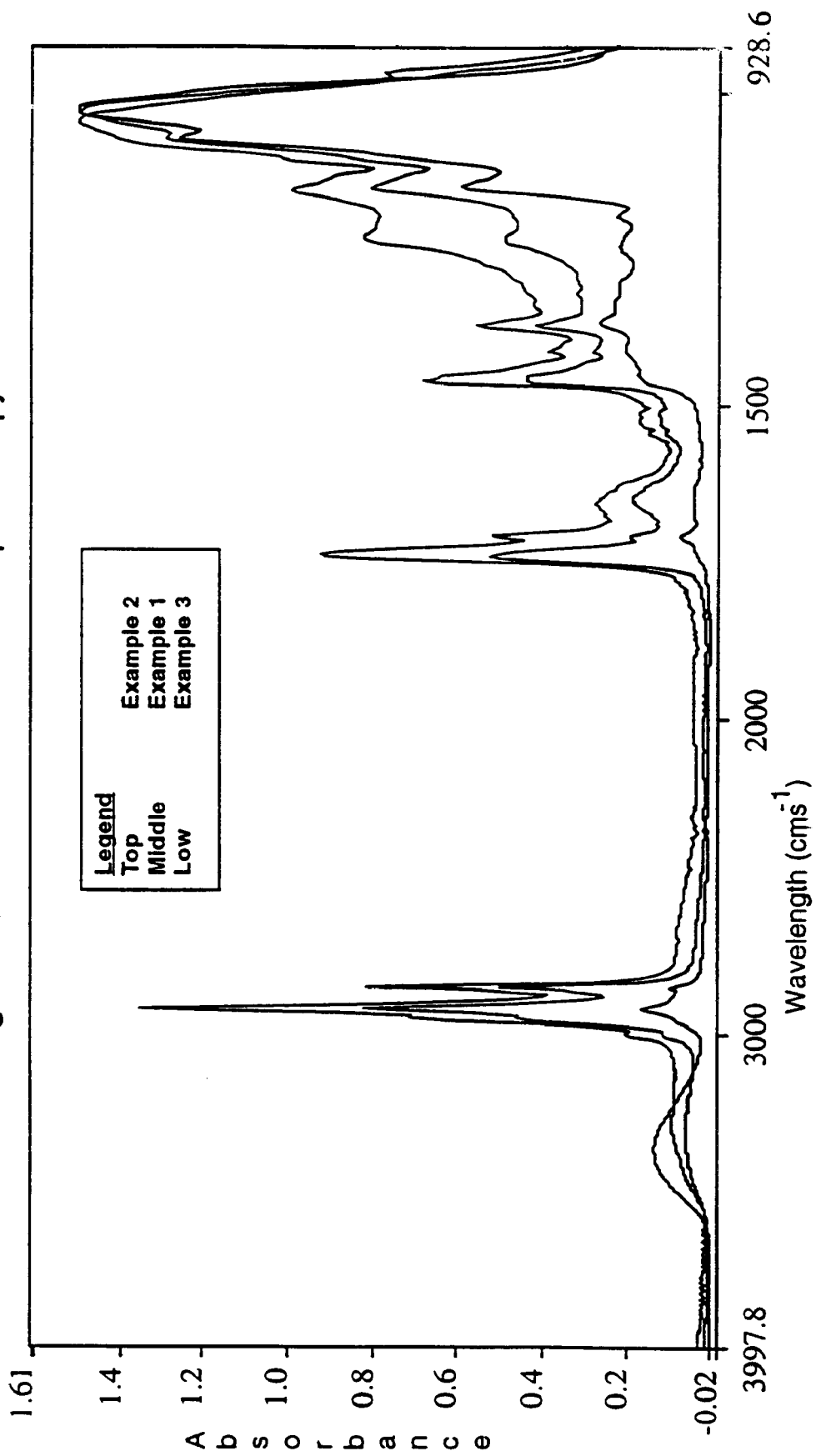

PRODUCTION OF β-GLUCAN-MANNAN PREPARATIONS BY AUTOLYSIS OF CELLS UNDER CERTAIN PH, TEMPERATURE AND TIME CONDITIONS

This invention relates to biologically active β-glucan-mannan preparations and to methods for their isolation. In particular, the invention relates to β-glucan-mannan preparations including β (1-3) glucan, produced from microorganisms including but not limited to yeasts, and to methods for producing the β-glucan-mannan preparations which avoid the use of concentrated alkali or acid.

BACKGROUND OF THE INVENTION

Polysaccharides are widely distributed in nature, and are particularly important for their role in maintaining the structural integrity of bacterial fungal, and plant cells. Glucans are polymers of D-glucose, and the D-glucose units may be linked together in a variety of ways. For example, glucans with 1-3, 1-4, 1-6, and 1-2 linkages are all known. The variety of linkages possible means that glucans are normally highly branched compounds. Because of their chemical properties, glucans have found a wide variety of uses in the chemical, food and pharmaceutical industries. For example, they are useful as viscosity imparting agents, emulsifiers, fibers, films, coating substances, supports for affinity chromatography and gel electrophoresis, in cell culture media, as filter pads, and in cement. They are also widely used as food thickeners and as a source of dietary fibre, and as carriers and coating agents in pharmaceutical products.

Glucans, particularly β (1-3)-glucans, have been very extensively studied, and in addition to the foregoing, have been shown to have a variety of pharmacological activities, including but not limited to anti-cholesterolaemic activity, hypoglycaemic activity, acceleration of heavy metal excretion, and stimulation of the immune system. The immunostimulatory activity of β-glucans has led to suggestions that they are useful as anti-cancer agents or in the treatment of HIV infection, as agents for stimulation of wound healing, or as anti-infective agents for use either alone or in conjunction with antibiotics.

The β-glucans can also induce the resistance response to disease in plants, such as phytoalexin production and wilting. This has led to suggestions that they can be used as anti-infective agents and growth promoters in plants.

Because of the problems entailed in intensive poultry, animal, fish or crustacean production, the use of β-glucans as an additive to these feeds, to reduce incidence of infection and consequently to promote growth and to reduce the need for antibiotics, has also been proposed.

β (1-3)-glucan is an important cell wall component of yeast cells. The cell wall of *Saccharaomyces cerevisiae* is primarily composed of β-linked glucan, which is mainly a backbone of β (1-3)-linked glucose units, with a minor component of inter and intra molecular branching via β (1-6)-linkages. Because of the very wide use of yeasts in the food and brewing industry, as well as in the production of industrial-grade alcohol, spent yeast cells are a major industrial by-product. Yeast-derived products themselves have considerable. commercial value, for example in such products as yeast extracts, flavouring agents, flavour potentiators such as guanosine monophosphate and inosine monophosphate, and in the manufacture of enzymes, fine chemicals and products for use in the biochemical and pharmaceutical industries, such as trehalose, thymidine, nucleosides and nucleotides, etc. Waste yeast from the brewing industry is a major source of β-glucans.

In addition, other species of yeast are also useful as a source of β-glucans, including but not limited to other yeast strains of *Saccharomyces cerevisiae, Kluyveromyces fragilis*, and Candida strains such as *Candida utilis*. All of these yeast strains can be produced using culture in food grade nutrients either by batch fermentation or continuous fermentation. Many other species of microorganisms, including bacteria, fungi and unicellular algae, have been reported in the art as a source of β-glucans.

The purification of β-glucans from yeast and other organisms has been extensively investigated, and a variety of methods is known. Most of these rely on the insolubility of β (1-3)-glucan in alkali or in organic solvents. The principal known methods are:

(a) High temperature extraction with concentrated sodium hydroxide, followed by high temperature extraction with acid and precipitation with ethanol (see for example Manners, D. J. et al., Biochem. J. 135 19–30 (1973), Jamas, S. et al., U.S. Pat. Nos. 4,810,646, No. 5,028,703, and No. 5,250,436 and Australian Patent No. 628752. by Phillips Petroleum Company). Many of these protocols require preliminary homogenisation of the yeast cells, and many require multiple repetition of each extraction step.

(b) Extraction with concentrated sodium hydroxide, followed by high temperature acid extraction and enzyme treatment to modify or purify the glucan (see for example Czech Patent Application No. 890038 by Masler, L. et al. which reports purification of β-D-glucan by alkali-acid extraction, followed by treatment with enzymes having amylase activity).

(c) Extraction of yeast cell wall preparations resulting from autolysis or enzyme degradation of yeast with concentrated phenol: water (1:1) (see for example U.S. Pat. No. 4,138,479 by Truscheit, E. et al.).

(d) Extraction with organic solvents such as isopropanol, ethanol, acetone, or methanol either alone or in the presence of alkali (see for example Japanese Patent publications No. 7051081, 6340701, 5295003, and 3002202; European Patent Application No. 515216).

Acid treatment is known to reduce the number of β (1-6)-linkages in the glucan material and this results in an increase in viscosity.

The cell wall of yeast is mainly composed of:

(i) fibrillar, alkali insoluble β (1-3)-linked glucan, with side branches of β (1-6)-linked glucan.

(ii) alkali-soluble β (1-3)-linked glucan with side branches of β (1-6)-linked glucan.

(iii) amorphous acid-soluble β (1-6)-glucan, with intermittent β (1-3)-linkages.

(iv) amorphous alkali-soluble mannan linked to proteins.

The fibrillar glucan component is located adjacent to the yeast plasma membrane, and is covered externally by an amorphous layer composed mainly of mannoproteins (Kopecka M. et al., J. Cell Biol., 62 68–76 (1974)). Particulate material (zymosan) isolated from the cell walls of *Saccharomyces cerevisiae* is known to have the ability to act as a non-specific immune stimulant. The biological activity of yeast cell wall particulates is largely attributed to the presence of β (1-3)-linked glucan, but the other two forms of glucan and mannan also have some ability to stimulate the immune system. Mannan is reported to mediate the adsorption and phagocytosis of particulate material, such as insoluble β (1-3)-glucan, by cells of the immune system (Giaimis, J., et al., Journal Of Leukocyte Biology 54 564–571 (1993); Sun-Sang, J., et al., Journal Of Cell Biology 96 160–166 (1983)).

Existing methods to isolate the β-glucans commonly use a multi-step alkali-acid extraction process (Manners, D. J., et al., J. Gen. Micro. 80 411–417 (1974)). The alkali extraction steps remove most of the amorphous mannoprotein and glucan material, and the subsequent acid extraction steps remove the glycogen and most of the β (1-6)-side branches from the fibrillar predominantly β (1-3) linked glucan. A final solvent extraction step is sometimes used to remove lipids.

It is clear that, given the retail price of glucan for some applications, the cost of producing glucan using existing published or patented methods is not commercially viable. These methods have the following problems:

(i) They are aimed at only producing the fibrillar, alkali-insoluble form of glucan. Other forms of glucan and the mannan present in the cell wall are removed as by-products of the process. These represent an additional amount of glucan, which could have significantly increased the glucan yield, and which may be functionally important.

(ii) The existing processes require significant capital investments.

(iii) The existing processes are hazardous, because of the requirement for high concentration caustic and acid treatments at high temperatures.

(iv) The processes result in a solution containing an alkali-insoluble glucan, which is difficult to separate based on conventional techniques, and this results in poor recoveries.

(v) The cost of production is high when compared to the value of the products in many applications.

Electron microscope studies of yeast cell walls (Kopecka M., et al., J. Cell Biol., 62 68–76 1974). showed that the fibrillar component of the cell wall was revealed when the outer amorphous layer of mannoproteins was removed by treatment with enzymes.

There is a clear need in the art for a rapid and inexpensive method of β-glucan extraction which avoids the use of high concentrations of alkali or acid and the use of high temperatures, which avoids loss of alkali soluble glucans and mannans, which has improved recovery of glucans and mannans and which results in a biologically active preparation.

We have now surprisingly found that a β-glucan-mannan preparation can be isolated using a simple autolysis process, at near-neutral pH and only slightly elevated temperature, and that excellent yields of a product with high immunostimulatory activity which may include stimulation of phagocytic activity, superoxide production, increased resistance to pathogens and infections, are obtained. Autolysis may be supplemented by treatment under gentle conditions with enzymes or other agents and if desired, the properties of the glucan-mannan product can be modified by acid treatment, degree of homogenisation or by varying the type of enzyme used.

BRIEF DESCRIPTION OF THE DRAWING

FIG. 1 depicts Fourier-Transform Infrared spectra of various glucan preparations, including a preparation made according to the disclosed invention.

SUMMARY OF THE INVENTION

According to a first aspect, the invention provides a method of production of an immunostimulatory β-glucan-mannan preparation, comprising the step of autolysis of cells of a microorganism at a pH of 5 to 6 and a temperature of 35 to 60° C. for 6 to 48 hours, prior to separating solid material from the autolysed product.

In a second aspect, the invention provides an improved method for the production of an immunostimulatory glucan-mannan preparation from cells of a microorganism, comprising the step of subjecting the said microorganism to a condition which causes autolysis; characterised in that the said condition comprises of incubation of the microorganism at a pH of 5 to 6 and a temperature of 35 to 60° C. for 6 to 48 hours, prior to separating solid material from the autolysed product.

In a third aspect, the invention provides an environmentally sound method for the production of an immunostimulatory β-glucan-mannan preparation from cells of a microorganism, the improvement comprising the step of subjecting the said microorganism to a mild condition which causes autolysis; wherein the said condition comprises of incubation of the microorganism at a pH of 5 to 6 and a temperature of 35 to 60° C. for 6 to 48 hours, prior to separating solid material from the autolysed product.

In a fourth aspect, the invention provides an economical method for the production of an immunostimulatory β-glucan-mannan preparation, using the conditions as described above to cause autolysis of the cells of the microorganism.

The incubation conditions provided in accordance with the method described above enables a potent immunostimulatory preparation comprising of glucans and mannan to be prepared inexpensively, efficiently and in a non-hazardous manner.

In a particularly preferred embodiment, the method described above leads to the production of an immunostimulatory preparation comprising of β (1-3)-glucan, more preferably of a β (1-3)-glucan-manna preparation.

The cells of microorganisms used in the method is also preferably subjected to further autolysis in the presence of one or more agents selected from the group consisting of sodium chloride, ethanol, proteolytic enzymes mannanase, amylase, and β-glucanases at a pH of 4 to 6 and a temperature of 35 to 60° C. for 6 to 48 hours, and separation of solid material from the autolysed product.

If desired, the enzymes can be used after the initial autolysis of the cells. That is, autolysis is conducted as a further step in the presence of one or more agents selected from the group consisting of proteolytic enzymes, mannanase, amylase and β-glucanases, prior to separating the solid material from the autolysed product.

Preferably, the autolysis is conducted at a temperature of 50 to 60° C., and for 18 to 24 hours.

In one particularly preferred embodiment the immunostimulatory potency of the β-glucan-mannan preparation thus produced is further improved by acidification to a pH of 2 to 4; even greater improvement is achieved by acidification to a pH of 2 to 4 followed by heat treatment. The preparation stimulates the immune system preferably by increasing phagocytic activity or the non-specific response.

More preferably, the immunostimulatory potency and viscosity of the β-glucan-mannan preparation thus produced is further increased by reducing the particle size of the extracted material to below 2 micron, more preferably, less than 1 micron, by using a mechanical disruption process such as milling, ultrasonic treatment or pressure homogenisation.

In another embodiment, milled yeast is used to obtain the β-glucan-mannan preparation. Yeast cells are subjected to autolysis and enzymatic digestion either during or following the milling phase, using conditions as described above.

In an alternative particularly preferred embodiment, the immunostimulatory potency and viscosity of the β-glucan-mannan preparation is altered by changing the nature of the enzyme used in the extraction process.

While spent yeast from the fermentation industry is especially useful in the process of the invention, it will be clearly understood that the invention is applicable to any source, such as microbial or plant material, in which β-glucans are present in a significant proportion. Microorganisms which have been reported to be useful sources of β-glucans include but are not limited to bacteria, such as Alkaligenes, especially *Alkaligenes faecalis* Var. mixogenes (ATCC-21680); Agrobacterium; Cellulomonas, such as ATCC 21399 and *Cellulomonas flavigena* (ATCC 53703); and Pestalotia; fungi, for example Aureobasidum such as *Aureobasidum pullulans* strain IFO446 and Aureobasidum species K-1 (FERM P1289); *Pleurotus ostreatus*; Macrophomopsis such as strain KOB55; Ganoderma; Schizophylla; *Fachyma hoelen*; Pestalotia; and Coriolus. In addition to brewing yeasts, other yeasts used in the food and fermentation industries are suitable for the purposes of the invention. These include but are not limited to yeasts used in the production of viscosity-imparting agents, emulsifiers, fibers, films, coating substances, supports for affinity chromatography and gel electrophoresis, in cell culture media, as filter pads and in cement. They are also widely used as food thickeners and as a source of dietary fibre, and as carriers and coating agents in pharmaceutical products.

The person skilled in the art will readily be able to determine the most suitable conditions under which the process of the invention can be applied to organisms other than yeast.

The person skilled in the art will be aware that for some applications of β-glucan and mannan the preparation produced using the method of the invention is advantageously provided in a dry form. The preparation is suitably dried by any suitable process, including but not limited to freeze-drying, roller drum drying, oven-drying, spray-drying, ring-drying or dried using film-forming equipment, and either may be used without further processing, or may be milled using any suitable technique to a particle size preferably of less than 20 micron. For other applications, a wet product such as a viscous paste, is suitable, and the preparation can be used either without further processing or following mechanical disruption to increase its viscosity and to reduce particle size.

According to a fifth aspect, the invention provides a β-glucan-mannan preparation produced by the process of the invention. the glucan-mannan preparation according to the invention preferably comprises mainly glucan (for example up to 80%) and some mannan (for example, up to 50%). The preparation may comprise of β 1-2, β 1-3, β 1-4 and β 1-6 glucans.

The preparation may be used alone. However, most commonly it will be provided in conjunction with other components. Thus, in this aspect of the invention, preferred embodiments include but are not limited to a poultry, fish, crustacean or shellfish feed composition comprising the β-glucan-mannan preparation of the invention, together with one or more veterinarily acceptable food components; an immunostimulatory, anticholesterolaemic, hypoglycaemic, or heavy metal excretion stimulating composition, comprising the β-glucan-mannan preparation of the invention together with a pharmaceutically acceptable carrier; a pharmaceutical composition comprising a pharmaceutically active agent and the β-glucan-mannan preparation of the invention as either a carrier or an adjuvant or as a coating for a solid dosage for such as a tablet or capsule; and a plant protection composition comprising the β-glucan-mannan preparation of the invention, together with an agriculturally acceptable carrier, and optionally an agriculturally acceptable nutrient or pesticide. The β-glucan-mannan preparation can also be supplied in drinking water to poultry or animals, or in ambient water to fish, crustaceans or shellfish.

It will be clearly understood that the preparation of the invention is generally suitable for use in products for which β-glucans are known to be useful. In same cases further purification may be desirable or necessary, and if so purification steps known per se may be used.

DETAILED DESCRIPTION OF THE INVENTION

The invention will now be described in detail by way of reference only to the following non-limiting examples.

EXAMPLE 1

Autolytic Extraction

A yeast sample was subjected to an autolytic extraction process. 1 Liter of the spent brewer's yeast (15% dry weight) was incubated for 6 to 48 hours at 35 to 60° C., with stirring. The pH was adjusted to between 5 and 6 using 2M NaOH or 2M HCl as necessary. These conditions promote yeast autolysis and the release of cell wall degrading enzymes. The material was centrifuged (3000 g, 4 to 20° C. for 15 minutes) and the sediment was washed with an equal volume of water before spray—or freeze-drying.

EXAMPLE 2

Enzymatic Extraction

The production of glucan-mannan by the autolytic extraction procedure of Example 1 was modified by the addition of substances known to induce yeast autolysis.

1 Liter of spent brewer's yeast (15% dry weight) was treated by the enzymatic process of Example 1. Further autolysis was induced by the addition of proteolytic enzymes (Papain, Optimase® APL440 (Solvay), Protmex® (Novo) and/or mannanase (Gist Brocades) and/or alpha amylase(Optidex L300 (Solvay),Ban 240L (Novo)) and/or glucanase (SP299 (Novo), Tunicase (Solvay). The pH was adjusted to the optimum pH for enzyme activity by using 2M NaOH or 2M HCl as necessary. The yeast was incubated for 6 to 48 hours at 35 to 60° C., with stirring. The material was centrifuged (3000 g, 4 to 20° C. for 15 minutes) and the sediment was washed with an equal volume of water. The sediment was dried as described earlier.

Glucanase (SP299) from Novo Enzyme Process Division contains an enzyme complex, produced by submerged fermantation of the fungus *Trichoderma harzianum*. The main activity of the preparation attacks the 1,3-α linkages of the insoluble glucan, called mutan. In addition, SP299 has cellulase, laminarinase, xylanase, chitinase, and proteinase activities.

Optimase® APL440, from Solvay Enzymes, is a bacterial alkaline protease (E.C. 3,4,21) produced by the fermentation of *Bacillus licheniformis*, and is an endopeptidase capable of hydrolyzing the interior peptide bonds of protein molecules.

Tunicase, from Solvay Enzymes, is a yeast cell wall enzyme produced by the controlled fermentation of an Arthrobacter species. The enzyme is characterized by its ability to hydrolyze the cell wall of yeast cells. The main enzymatic component of Tunicase is β-1,3-glucanase (β-1,3-glucanlaminaripentaohydrolase).

Optidex, from Solvay Enzymes, is a glucoamylase (amylglucosidase) of food grade quality produced by a selected strain of Aspergillus niger. Being an exoenzyme it cleaves glucose molecules from the non-reducing end of liquefied starch, amylose, amlyopectins or maltodextrins.

Protamex™, from Novo Nordisk, is a Bacillus protease complex developed for hydrolysis of food proteins. The optimal working conditions are at a pH of 5.5–7.5 and at 35–60° C.

BAN (Bacterial Amylase Novo), from Novo Nordisk, is an α-amylase produced by submerged fermentation of a selected strain of Bacillus amylolichenfaciens. The systematic name is 1,4-α-D-glucan glucano hydrolase (EC 3.2.1.1).

EXAMPLE 3

A Comparison of Glucan Produced by the Prior Art (Alkali-acid) Process with Glucan-mannan Produced by the Methods of the Present Invention (Autolytic and Enzymatic)

For comparative purposes, a sample of purified β (1-3) glucan was prepared using an alkali-acid extraction process based on that of Manners, D. J., et al., Biochemical Journal 135 19–30 (1973).

1 Liter of spent brewer's yeast (20% dry weight) was extracted with an equal volume of sodium hydroxide (4% w/v) at 100° C., for 3 hours with stirring, to remove the mannoproteins. The material was centrifuged (3000 g for 15 minutes at 4° C.), the supernatant discarded and the pellet extracted a further 4 times with sodium hydroxide (4% w/v). The sediment from the final caustic extraction stage was washed twice with water (2L) and extracted with acetic acid (0.15m), at 100° C., for 3 hours with stirring, to remove glycogen. The material was centrifuged (3000 g for 15 minutes at 4° C.) and the acid extraction stop was repeated a further 3 times. The sediment from the final acid step was washed twice with water (2L) and then with 15 mL of ethanol 96% v/v). The material was centrifuged (3000 g for 15 minutes at 4° C.) prior to spray drying or freeze-drying the material.

Samples prepared using the prior art method (described above) or commercially available samples of glucan prepared by alkali-acid extraction were compared to glucan prepared according to the present invention.

Proximate analysis was carried out according to the Official Methods Of Analysis of the Association of Official Analytical Chemists, methods 27.8.04, 27.6.08, 32.1.14 (mod), 27.8.05, Sixteenth Edition, 1995. The results of these analyses are presented in Table 1.

TABLE I

A Comparison of Glucans Produced by the Alkali-Acid, the Autolytic and Enzymatic Procedures: Proximate Analysis

| Analysis (% on a dry weight basis) | Alkali-Acid Glucan | Antolytic Glucan | Enzymatic Glucan |
|---|---|---|---|
| Ash | 3 | 2 | 3 |
| Fat | 4 | 4 | 6 |
| Protein | 1 | 27 | 20 |
| Carbohydrate | 90 | 66 | 71 |

The glucan produced by the prior art method (alkali-acid) was shown to have less protein and more carbohydrate in comparison to samples produced by the present method as shown in Table I.

Fourier-Transform Infrared (FTIR) spectra of the glucan preparations were recorded using a Perkins-Elmer spectrophotometer. The samples were freeze dried to remove any residual moisture, slurried in tetrachloroethylene and analysed on a horizontal attenuated total reflectance (ATR) cell. The complete spectrum is shown in FIG. 1.

The FTIR spectra of samples prepared by the prior art (alkali-acid) differed from the spectra of samples prepared by the present method (autolytic or enzymatic an shown in FIG. 1). The samples prepared by the prior art method lacked strong absorption in the 2955 to 2855 cms$^{-1}$ (indicative of saturated fatty acids), 1744 cms$^{-1}$ (indicative of glycosides), 1650 cms$^{-1}$ (indicative of protein). The spectra of the glucan sample prepared by the prior art method (alkali acid) was solar to the spectra of a purified β-glucan preparation with strong absorbance in the 950 cm$^{-1}$ band.

The mount of glucan and mannan in the samples prepared by the prior art (alkali-acid) and present method (autolytic and enzymatic) were determined by selective extraction and colorimetric analysis (based on Stewart, P. R., Methods In Cell Biology XII 111–145 (1975)). The glucan samples prepared by the prior method contain little mannan in comparison to the samples prepared by the present method as shown in Table II.

The samples were also hydrolysed and analysed by gas chromatography, to identify the sugar components. The samples were hydrolysed using 4M trifluoroacetic acid for 4 hours at 100° C. under argon. The acid was removed by evaporation under a nitrogen stream, following which the samples were reduced and acetylated as described in Harris, P. J. et al., Carbohydrate Research 127 59–73 (1984). The hydrolysates were analysed by gas chromatography on a BPX70 column using flame ionisation detection. The injector and detector temperature were 280 and 300° C., respectively. The oven was held at 185° C. for 1 minute and then ramped at 3° C. per min to 260° C. and held at the final temperature for 5 minutes.

The glucan samples prepared by the prior art method showed peaks corresponding only to glucose, indicating that the carbohydrate component was mainly glucans as shown in Table II. Samples prepared by the present method contained glucose as well as a substantial amount of mannose sugars, indicating that the carbohydrate component was a mixture of mannan and glucans. Insoluble β (1-3)-glucans are relatively resistant to acid hydrolysis in comparison to mannan: thus the gas chromatographic method underestimates the concentration of glucose (and therefore glucan) in comparison to the colorimetric method.

TABLE II

A Comparison of Glucans Produce by the
Alkali-Acid and the Autolytic and
Enzymatic Procedures: Carbohydrate Analysis

| Analysis (% w/w) | Alkali-Acid Glucan | Autolytic Glucan | Enzymatic Glucan |
|---|---|---|---|
| glucan colorimetric assay | 88 | 48 | 54 |
| mannan colorimetric assay | 1 | 9 | 8 |
| glucose GC assay | 65 | 50 | 45 |
| mannose GC assay | not detected | 25 | 15 |

The types of linkages between the glucose residues in glucan samples prepared using the alkali-acid extraction and present method (autolytic and enzymatic) were determined by methylation analysis using a procedure based on that of Harris, P. J. et al., Carbohydrate Research 127 59–73 (1984).

The results in Table III show that the sample prepared by the alkali-acid method was composed mainly of (1-3)-linked glucose in comparison to the samples prepared by the method according to the present invention.

TABLE III

Comparison of Glucans Produced by the Alkali-Acid,
Autolytic and Enzymatic Procedures: Linkage Analysis

| Linkage Analysis of glucose monomers. (relative percentages) | Alkali-Acid Glucan | Autolytic Glucan | Enzymatic Glucan |
|---|---|---|---|
| Terminal | 4 | 26 | 24 |
| 1-2 linked | 0 | 14 | 14 |
| 1-3 linked | 94 | 29 | 40 |
| 1-4 linked | 2 | 25 | 14 |
| 1-6 linked | 0 | 6 | 8 |

The glucan samples were tested for biological activity using a mouse model. The material produced by each of the three processes had a particle size of predominantly 100–300 micron. The dried material was milled in a bead mill to a particle diameter of <20 micron and was used to inject mice intraperitoneally (2 mg/mouse). After 72 hours, the cells induced into the peritoneal exudate were harvested from the peritoneal cavity, incubated with heat-killed yeast cells, and the percentage of phagocytic cells was calculated.

The material prepared in accordance with the present invention (autolytic or enzymatic) is more potent at inducing a non-specific immune response than the material prepared by the alkali/acid extraction procedure, as shown by an increase in the number of cells in the peritoneal cavity, due to a chemotactic effect of the injected material attracting inflammatory cells, and an increase in the number of phagocytic neutrophils and macrophages. These results are shown in Table IV.

TABLE IV

A Comparison of Glucans Produced by the
Alkali-Acid and the Autolytic and Enzymatic Procedures:
Ability to Induce Phagocytic Cells.

| Analysis | Alkali-Acid Glucan | Autolytic Glucan | Enzymatic Glucan |
|---|---|---|---|
| Cells in the peritoneal cavity ($\times 10^6$) | 11.9 | 11.9 | 15 |
| % phagocytic macrophages | 45 | 50 | 70 |
| % phagocytic neutrophils | 16 | 33 | 30 |

Without wishing to be bound by any proposed mechanism for the beneficial effect observed, we believe that mannan and non-$\beta$ (1-3)-linked glucan may act synergistically with the fibrillar $\beta$ (1-3)-linked glucan to produce a better immune response.

EXAMPLE 4

Improving the Potency of the Glucan-mannan Preparation by Acidification

1 Liter of spent brewer's yeast (15% dry weight) was treated by the enzymatic process of Example 1. An aliquot of the sediment was freeze-dried. The pH of the remaining sediment was adjusted to 2 to 4 with either hydrochloric or acetic acid and then the sediment was either freeze-dried or oven-dried at 80° C. The sugar linkages were analysed by GC-MS, as described in Example 3.

The glucan-mannan material was milled to <20 microns; and tested for ability to induce phagocytic cells, as described in Example 3. The results in Table V show that acidification followed by oven-drying improved the potency of the glucan-mannan at stimulating the immune response, and that acidification followed by heat treatment breaks down some of the $\beta$ (1-6)-linkages glucan, perhaps revealing more of the active sites in the microfibrillar glucan.

TABLE V

Effect of Heat-Drying Acidified Material

| Analysis | Freeze dried without acidification | Freeze dried following acidification | Oven dried following acidification |
|---|---|---|---|
| Cells in peritoneal cavity ($\times 10^6$) | 4.15 | 3.9 | 7.1 |
| % phagocytic macrophages | 55 | 52 | 68 |
| % phagocytic neutrophils | 43 | 41 | 50 |
| Ratio of $\beta$ (1-3) to $\beta$ (1-6) linkages in glucan. | 4.9:1 | 5.28:1 | 7.3:1 |

EXAMPLE 5

Improving the Potency of the Glucan-mannan Preparation by Altering the Particle Size It is known that the potency of some materials can be altered significantly by changing the particle size. 1 Liter of the spent brewer's yeast (10% dry weight) was treated by the enzymatic process of Example 1. The final sediment was suspended in water (20% dry weight). At this stage the glucan-mannan material appeared microscopically as discrete spheres of about 4 to 6 micron dieter. An aliquot of the suspended sediment was treated for 6 minutes in a Braun cell homogeniser using glass beads varying in diameter from 0.25 to 1 mm in bead size. This disrupted the glucan spheres to particles below 2 micron in size, and resulted in a highly viscous product with the consistency of whipped cream. The product when tested by the method described in Example 3 showed a good ability to stimulate a non-specific immune response.

In a variation of the method, freshly harvested yeast cells were bead milled to disrupt the cells. During or following the milling phase, the yeast cells were subjected to autolysis and enzymatic digestion using similar conditions to those described in Example 1 or 2. The insoluble material was harvested by centrifugation and tested for biological activity using the mouse model. The results are summarised in Table VI.

TABLE VI

Effect of Altering the Glucan Particle Size

| Analysis* | Whole glucan particles (4–6 micron) | Disrupted glucan particles (<1 micron) | Disrupted and then enzymatically digested yeast particles. (<1 micron) |
|---|---|---|---|
| % increase in cells/periton eal cavity | 150 | 250 | 250 |
| % increase in phagocytic macrophages | 50 | 118 | 125 |
| % increase in phagocytic neutrophils | 10 | 24 | 30 |

*Compared to dried yeast or dextran injected controls.

For the disintegration of the yeast or glucan particles, a number of other wet milling processes and equipment may be used. These include but are not limited to pressure homogenisation (Manton Gaulin), bead milling and ball milling (Dyno-mill, Drais mill, Netzsch mill).

EXAMPLE 6

Improving the Potency of the Glucan-mannan Preparation by Altering the Nature of the Enzymes Used A fresh yeast slurry (16.5% dry weight) was washed with water and was the incubated for 17 hours at 50° C. with stirring. The autolysed yeast was heated to 100° C. for 30 minutes and then divided into 2 batches.

One batch was treated with enzymes from Solvay. The yeast was incubated with 1% w/w Optimase APL-440 (proteolytic enzyme) for 2 hours at 47° C. and pH 9, with stirring. The pH was then reduced to 7.5, and 1% w/w Tunicase FN (glucanase) enzyme was added. After 6 hours incubation, 1% Optidex (glucoamylase) was added, and the mixture was further incubated for 6 hours at 60° C. and pH 4.5. A viscous sediment was obtained. The sediment was freeze dried and ball milled.

The second batch was incubated with enzymes from Novo. The yeast was incubated for 6 hours with 1% w/w BAN (glucoamylase) and 1% w/w Mutanase SP299 (glucanase) enzyme at pH 5.5 with stirring. 1% Protomex (proteolytic enzyme) was added, and the mixture was incubated at 55° C. and pH 5.5 for a further 16 hours.

In a different experiment, the glucan-mannan prepared according to Example 1 was treated with 1% w/w Tunicase (pH 7.5 at 35° C. for 6 hours). The glucan-mannan treated with Tunicase increased in viscosity. The preparation was centrifuged and the sediment was freeze dried and milled. The supernatant from the Tunicase-treated glucan was dialysed extensively against distilled water and freeze dried.

The types of linkages between the glucose residues in the glucan samples were analysed as described in Example 3. Biological activity was also tested using the mouse model. The results are shown in Table VII, which shows that enzymes can be used to alter the nature of the glucan preparation. For example treatment with Tunicase (Solvay) results in a viscous product with reduced β (1-6)-linkages in the glucan preparation. Enzymes can also be used to produce a biologically-active soluble form of glucan.

TABLE VII

Effect of Enzyme Activity

| Analysis* | Solvay Enzymes Process | Novo Enzymes Process | Tunicase Sediment | Tunicase Supernatant |
|---|---|---|---|---|
| Ratio of β (1-3) to β (1-6) linkages in glucan. | 25:1 | 4.6:1 | 5.4:1 | not determined |
| % increase in cells/peritoneal cavity. | 330 | 268 | 110 | 65 |
| % increase in phagocytic macrophages | 65 | 90 | 96 | 140 |

EXAMPLE 7

Altering the Viscosity of the Glucan-mannan Preparation

The viscosity of the glucan-mannan, prepared as described in Example 2, can also be altered by acidification (Example 4), by milling (Example 5) and by varying the type of enzyme used (Example 6). The viscosity was measured using a CSL100 rheometer with 60 mm plates. The measurements were taken at 20° C., at a shear rate of 100/s using a 10% w/v glucan suspension, and the results are summarised in Table VIII.

TABLE VIII

Altering the Viscosity of The Glucan-Mannan Preparation.

| Treatment | Viscosity (Pa · s) |
|---|---|
| Glucan prepared as in Example 2 with pH of 4.5. | $5.8 \times 10^{-3}$ |
| Glucan prepared as in Example 2, pH of 4.5 and boiled for 10 mins. | $7.82 \times 10^{-3}$ |
| Glucan prepared as in Example 2, pH of 4.5, boiled for 10 mins and milled to below 1 micron. | 1.10 |
| Glucan prepared as in Example 2, pH of 3, boiled for 10 mins and milled to below 1 micron. | 1.40 |
| Glucan Prepared as in Example 6 using Tunicase. | 1.50 |

Therefore, viscosity of the glucan-mannan preparation can be altered with heat, acid, enzymes and by changing the particle size, to produce a viscous material. This can be used as a cream, gel or the like.

EXAMPLE 8

Effectiveness of the Glucan-mannan Preparation as an Immmune Enhancer in Fish Rainbow trout (*Oncorhynchus mykiss*) were obtained from a commercial farm in Victoria. The fish had an average body weight of 13 g and were distributed among 6×260L experimental tanks, with 12 fish in each aquarium. The fish were acclimatised for 7 days prior to starting the experiment.

Standard trout pellets were used and the fish were fed twice daily at approximately 5% of the body weight per day. The glucan-mannan preparation was incorporated into the diet to give a final concentration of 0.1% w/w in the final feed. All diets including the control diet were repelleted and dried at 50° C. After 3 weeks on the feed the fish were anaesthetised with benzococaine (1:10,000) and sacrificed.

The pronephros were harvested into tissue culture medium containing 1 unit of heparin per mL. The tissue was teased through a stainless steel 80 gauge mesh sieve to isolate single cells. The cell suspensions were washed with Dulbecco's Modified Eagle's Medium (DMEM) (Gibco Laboratories). The cells were subjected to a nitroblue tetrazolium assay to detect production of the superoxide anion (based on Rook, J., et al., J. Immunol. Methods 82 161–167 (1985)) and to a phagocytosis assay to determine the ability of the macrophages to phagocytose yeast cells.

The glucan-mannan produced as described in Example 2 was found to increase the phagocytic activity and the production of the superoxide anion in cells isolated from the pronephros in rainbow trout, as shown in Table IX. The data show that the glucan-mannan produced as described in Example 2 can stimulate the immune system in rainbow trout.

TABLE IX

Effectiveness as an enhancer of the immune response in fish.

| Diet | % Phagocytosis. | Superoxide production |
|---|---|---|
| Control | 27.2 | 0.038 |
| Glucan-mannan preparation (Enzymatic method) | 37.1 | 0.068 |

EXAMPLE 9

Capacity of the Glucan-mannan Preparation to Reduce Mortality in Fish

Underyearling rainbow trout (*Oncorhynchus mykiss*) were obtained from a commercial farm in Tasmania. They had an average man body weight of 65 g. The fish were distributed among 6 insulated aquaria, with 16 fish in each aquarium. The fish were maintained at an air temperature of 15° C. and a water temperature of 13–18° C., and were acclimatised for 7 days prior to starting the experiment.

The fish were fed daily to satiation with Gibson's trout pellets at approximately 2.5% of body weight per day. The glucan preparations (either glucan prepared according to Example 2 or a glucan produced using the alkali/acid extraction process) were incorporated into a 5% w/w gelatin solution and coated on to the pellets to provide a concentration of 0.1% w/w glucan in the final feed. Pellets fed to the control fish were coated with gelatin only. The following feeding schedule was utilised :14 days on supplemented feed, followed by 42 days on unsupplemented feed, and then another 14 days on supplemented feed. One week after the second period of supplementation the fish were challenged with *Vibrio anguillarum*.

A Tasmanian strain of *V. anquillarum* serotype C (equivalent to serotype 01) was used (Munday, B., et al., Immunology and Cell Biology 70 391–397(1992)). The organism was grown in a nutrient broth medium supplemented with 2% NaCl.

The fish were challenged with *V. anguillarum* by injecting $3 \times 10^7$ c.f.u. ($LD_{50}$ dose) of the organism intraperitoneally, and were observed at least twice daily for 10 days. All fish which died were cultured for *V. anguillarum*.

Deaths occurred during the three days following inoculation. On the 3rd and 4th day following inoculation, many of the control groups were lethargic and had hyperaemia at the base of the fins and on the belly, although no further mortalities were record in this group.

Following challenge with *V. anguillarum*, the protective effect of the glucan according to the invention was evident. A glucan prepared using the alkali-acid extraction process was less effective, as shown in Table X.

TABLE X

Ability of glucan-mannan to reduce mortality in fish

| Diet | % Mortality 10 days after the challenge. |
|---|---|
| Control | 15.6 |
| glucan preparation (enzymatic method) | 3.1 |
| glucan preparation (alkali/acid method) | 9.4 |

The results indicate that the glucan-mannan produced as described in Example 2 can be used to improve the resistance of rainbow trout to infection by *Vibrio anguillarum*, and is superior to a prior art glucan preparation.

EXAMPLE 10

Ability of the Glucan-mannan Preparation to Reduce Mortality in the Shrimp *Penaeus monodon*

5–10 g *P. monodon* shrimps were obtained from a farm in Queensland. 12 shrimps were weighed into 12×60L aquaria. The shrimps were acclimatised for 5 days in the aquaria and then fed control or treatment diets. After 23 days, the shrimps were injected with an $LD_{50}$ dose of *Vibrio harveyi*. The mortalities were monitored for 7 days. During this period the shrimps were fed on either the control or treatment diet.

All shrimps were fed on a steam pelletised standard diet (CP 100). Glucan-mannan according to the present invention was added to the treatment diet by adhesion with gelatin to the surface of the pellet. A solution of approximately 5% w/v gelatin solution was prepared and mixed into the control diet at the rate of 100 ml/kg of pellet. The gelatin solution used for the treatment diet contained enough glucan-mannan prepared according to Example 2 or a glucan produced using the alkali/acid extraction process to ensure a final concentration of 0.1% w/w in the final diet. The feeding rate was 6.5 to 5% of shrimps body weight/day.

A pathogenic strain of *V. harveyi*, strain 656 isolated from a moribund *P. esculentus* shrimp, was used for challenge studies. The bacteria were subcultured overnight at 26–28° C. in Seawater Liquid Broth with vitamins. The cells were washed three times with 0.73% w/v saline solution with centrifugation at 2,000 rpm, at 40° C. for 30 minutes. Vortex mixing was used at each step. Serial dilutions of the bacterial suspension was prepared, and each dilution was injected into untreated prawns in order to calculate the $LD_{50}$ dose. From each serial dilution, 0.1 mL was mixed with 25 ml of 42° C. Marine Agar with vitamins (MAV) and poured into Petri dishes. After 24 hours at 26–28° C. the colonies were counted and the number of bacteria in each of the inoculation suspension was calculated. The pour plates were used to calculate the number of bacteria in the injection volume of 0.05 ml.

Strain 656 *V. harveyi* injected at a dose of 1–2×10$^5$ in 0.05 ml was finally selected for the $LD_{50}$ challenge. The shrimps were injected in the second abdominal section. Mortalities were recorded on a daily basis for the next seven days, mortality percentages were calculated as follows:

$$\% \text{ of mortality} = \frac{\text{Number of dead shrimps} - A}{\text{Total number of shrimps} - A} \times 100.$$

A=mortality after day 1.

The performance and health of the shrimps were monitored in the feeding stage prior to challenge with *V. harveyi*. While there was no significant effect on growth, the shrimps on the diet of glucan-mannan prepared as described in Example 2 had better appetites were more lively and showed a lower incidence of mortality.

Following challenge with *V. harveyi*, the protective effect of the glucan of the invention was evident. Glucan prepared according to the alkali/acid method was less effective, as shown in Table XI.

TABLE XI

Reduction in mortality in shrimps.

| Diet | % Mortality 7 days after the challenge. | Number of shrimps used for challenge |
|---|---|---|
| Control | 50 | 99 |
| glucan preparation (enzymatic method) | 11* | 92 |
| glucan preparation (alkali/acid method) | 18 | 55 |

*Significantly different from the control group.

The glucan-mannan prepared as described in Example 2 can therefore be used to successfully improve the disease resistance of the shrimp *P. monodon*.

EXAMPLE 11

Capacity of Glucan-mannan Preparation to Enhance Disease Resistance in Poultry

Two hundred and forty mixed sex broiler chickens were allocated amongst 4 different dietary treatments. The day old broiler chicks were housed in two battery brooders and were uniformally allocated to the 24 compartments at 10 chicks per compartment. The chicks were fed with either a standard non-medicated commercial diet (control) or a standard diet with glucan-mannan incorporated into the feed at 1 g/kg feed. The glucan-mannan was either prepared according to the method in Example 2 or Example 5 (enzyme action during or following milling). The chicks were offered the diets ad libitum between one day and 21 days of age. The growth rates were monitored at weekly intervals.

At the conclusion of the feeding trial, 18 birds from each treatment were bled. The blood was collected in heparinised tubes and washed twice with PBS. The bactericidal activity of circulating blood leucocytes was assessed by isolating leucocytes from a small blood sample and incubating with a viable suspension of *Staphylococcus aureus*. After the 1 hour incubation period, the blood cells were lysed and the number of viable bacteria was measured.

Another 20 birds from each treatment were transferred to bubble isolators, with one treatment group per isolator. Cloacal swabs taken from each bird confirmed that the birds were Salmonella-free. The feed was irradiated to ensure it was Salmonella-free. The birds were orally inoculated with an engineered strain of *Salmonella typhimurium* (nalidixic acid resistance). Five birds from each treatment were sacrificed at varying time intervals, and Salmonella counts were taken from the gastrointestinal tract. Results are summarised in Table XII and Table XIII.

TABLE XII

Effect of glucan-mannan preparation on poultry health: growth rates and monocyte activity.

| Treatment | Day 21 weight (g) | Viable bacteria (cfu/mL) |
|---|---|---|
| Control | 799 | $2.3 \times 10^4$ |
| 0.1% glucan (enzymatic method) | 813 | $1.2 \times 10^4$ |
| 0.1% glucan milled and then digested enzymatically | 818 | $7.7 \times 10^3$ |

TABLE XIII

Challenge trials: Salmonella colonisation

| Analysis | Control | 0.1% glucan (enzymatic method) | 0.1% glucan milled and then digested enzymatically |
|---|---|---|---|
| % of birds colonised after 2 days | 93 | 0 | 60 |
| % of birds colonised after 4 days | 100 | 60 | 20 |
| Salmonella numbers (CFU/g) at 2 days | 2364 | 0 | 760 |
| Salmonella numbers (CFU/g) at 4 days | 30000 | 15840 | 6000 |

Table XII shows that glucan-mannan produced a 2–3% improvement in growth rates. The glucan-mannan preparation boosts the immune response in broiler chickens and enhances the ability to resist infection whereas Table XIII shows that the addition of glucan-mannan to the diet significantly reduced the incidence and the extent of colonisation by Salmonella in broiler chickens.

EXAMPLE 12

Functional Beverages

The glucan-mannan preparation according to the present invention can be added to drinks or food (e.g yoghurt) to improve the health of humans prone to infection such as immune-compromised individuals, athletes in intensive training, and, persons with hectic lifestyles or suffering from gastrointestinal tract problems. A suitable formulation for use as a non alcoholic beverage is:

25% juice content of carrot, tomato and/or orange

1% (w/v) glucan preparation.

In Summary:

(i) Our process for production of a particulate glucan preparation which contains mannan and with immunostimulatory activity differs considerably from the previously-known processes, which are based on alkali-acid, phenol: water, or solvent extraction.

(ii) The glucan-mannan material produced by our process is less pure than that produced by the alkali-acid extraction process, yet it is more potent in stimulating a non-specific immune response in mice.

(iii) The activity of the glucan-mannan material can be improved by acidifying the material prior to heat-drying.

(iv) The viscosity and biological activity of the glucan-mannan material can be altered significantly by altering the particle size, acid treatment and end treatment.

The glucan-mannan material of the present invention is useful in a number of areas, including, but not limited to:

i) Aquaculture: in order to increase the resistance of bony fish and crustaceans to various water-borne infections. The glucan material can be administered in prepared fish feed.

ii) Animal husbandry: the glucan material can be administered to animals and poultry in stock feed pet food and in a liquid form.

iii) Veterinary and medical uses: the glucan-mannan material may be administered as a topical wound-healing cream or film, or may be administered orally, intranasally or via parenteral injection.

iv) As a food supplement: Yeast cell wall material produced as a by product is already an approved food additive used as a thickener or to provide dietary fibre in salad dressings, soups, spreads, sauces etc., and in useful in "functional" foods and beverages to promote resistance to disease.

v) Cosmetics: in creams and lotions for example to reduce sunburn and formulations for sensitive skins.

vi) Pharmaceutical: As a wound-healing agent, anticancer agent, or anti-infective agent in immune suppressed patients or patients otherwise prone to infection. The product of the invention may be used in creams, lotions, tablets, mouthwashes or the material can be dried into a film for use as a wrapping for burns. It may be used as an adjuvant with vaccines, antibiotics or other pharmaceutical preparations.

It will be clearly understood that the glucan-mannan product of the invention is applicable to uses of β-glucans which have been described in the prior art.

It will be apparent to the person skilled in the art that while the invention has been described in some detail for the purposes of clarity and understanding, various modifications and alterations to the a embodiments and methods described herein may be made without departing from the scope of the inventive concept disclosed in this specification.

The claims defining the invention are as follow:

1. A method of production of an immunostimulatory preparation that contains β-glucans and mannans, wherein the β-glucans comprise 1,3-β-glucans and 1,6-β-glucans, comprising the steps of:

a) subjecting cells of a microorganism to a first autolysis step at a pH of about 5 to about 6 and a temperature of about 35 to about 60° C. for about 6 to about 48 hours to produce a material with a particle size of from about 100 to 300 microns;

b) separating solid material from the autolysed product;

c) subjecting the solid material of step (b) to a second autolysis step in the presence of one or more agents, selected from the group consisting of a proteolytic enzyme, mannanase, amylase, and β-glucanase, at a pH of about 4 to about 6 and a temperature of about 35 to about 60° C. for about 6 to about 48 hours, d) separating the solid material from the autolysed product, and then e) reducing the solid material to particles of less than about 2 microns.

2. A method according to claim 1, wherein the first autolysis step is performed at a temperature of about 50 to about 60° C.

3. A method according to claim 1, wherein the autolysis is carried out for 18 to 24 hours.

4. A method according to claim 1, wherein the first autolysis is carried out in the presence of an agent selected from the group consisting of sodium chloride, ethanol, a proteolytic enzyme, mannanase, amylase, and β-glucanases.

5. A method according to claim 1, wherein the proteolytic enzyme is selected from the group consisting of a bacterial alkaline protease produced by fermentation of *Bacillus licheniformis* and a protease composition isolated from a Bacillus species.

6. A method according to claim 1, wherein the β-glucanase is selected from the group consisting of a yeast cell wall degrading enzyme produced by the fermentation of an Arthrobacter species and an enzyme complex produced by fermentation of *Trichoderma harzianum*.

7. A method according to claim 1, wherein the amylase is selected from the group consisting of a glucoamylase produced by a strain of *Aspergillus niger* and an α-amylase produced by fermentation of a strain of *Bacillus amylolichenfaciens*.

8. A method according to claim 1, wherein the β-glucan and mannan preparation is further subjected to acidification to a pH of about 2 to about 4.

9. A method according to claim 8, wherein the acidification is followed by heat treatment.

10. A method according to claim 1, wherein the viscosity of the β-glucan and mannan preparation is changed by reducing the particle size of the preparation to less than 1 micron.

11. A method according to claim 10, wherein the disruption process is selected from the group consisting of milling, ultrasonic treatment and pressure homogenization.

12. A method according to claim 7, wherein the immunostimulatory potency and viscosity of the β-glucan and mannan preparation is altered by using different proteolytic enzymes in the production process.

13. A method according to claim 1, wherein the microorganism is selected from the group consisting of yeast, bacteria and fungi.

14. A method according to claim 13, wherein the yeast is one which is used in the production of viscosity-imparting agents, emulsifiers, film coating substances, supports for affinity chromatography, supports for gel electrophoresis, cell culture medium, filter pad or cement.

15. A method according to claim 14, wherein the yeast is a species selected from the group consisting of *Saccharomyces cerevisiae, Kluyveromyces fragilis* and Candida.

16. A method according to claim 13, wherein the bacteria are of a genus selected from the group consisting of Alkaligenes, Agrobacterium, Cellulomonas, and Pestalotia.

17. A method according to claim 13, wherein th fungi are of a genus selected from the group consisting of Aureobasidum, Pleurotus, Macrophomopsis, Ganoderma, Schizophylla, Fachyme, and Coriolus.

18. A method according to claim 1, wherein the diameter of the solid material is less than about 1 micron.

19. A method according to claim 1, wherein the product comprises at least about 8% w/w of mannan.

20. A method according to claim 10, in which the particle size is reduced by using a mechanical disruption process.

21. A method of production of an immunostimulatory preparation according to claim 1, wherein the pH of the first autolysis step is 5 to 6, the temperature is maintained from 35 to 60° C. for 6 to 48 hours, and the diameter is less than about 2 microns.

22. A method according to claim 2, wherein the autolysis step is performed at a temperature of 50 to 60° C.

23. A method according to claim 1, wherein the autolysed product is subjected to a second autolysis step in the presence of one or more agents selected from the group consisting of a proteolytic enzyme, mannanase, amylase, and β-glucanases at a pH of 4 to 6 and a temperature of 35 to 60° C. for 6 to 48 hours, and the solid material is separated from the autolysed product.

24. A method according to claim 8, wherein the β-glucan and mannan preparation is further subjected to acidification to a pH of 2 to 4.

25. A method according to claim 1, wherein the product comprises 1,3-linked and 1,6-linked glucose monomers, and wherein the ratio of 1,3-linked to 1,6-linked-glucose monomers is 4.9:1 to 7.3:1.

* * * * *